United States Patent
Weiner et al.

(10) Patent No.: US 8,710,277 B2
(45) Date of Patent: Apr. 29, 2014

(54) PROCESS FOR MAKING DIETHYL ETHER FROM ACETIC ACID

(75) Inventors: Heiko Weiner, Pasadena, TX (US); Radmila Jevtic, Houston, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 538 days.

(21) Appl. No.: 12/850,414

(22) Filed: Aug. 4, 2010

(65) Prior Publication Data

US 2011/0098513 A1   Apr. 28, 2011

Related U.S. Application Data

(63) Continuation-in-part of application No. 12/588,727, filed on Oct. 26, 2009.

(60) Provisional application No. 61/300,812, filed on Feb. 2, 2010.

(51) Int. Cl.
*C07C 41/09* (2006.01)
*C07C 41/01* (2006.01)
*C07C 43/06* (2006.01)

(52) U.S. Cl.
CPC .............. *C07C 41/09* (2013.01); *C07C 41/01* (2013.01); *C07C 43/06* (2013.01)
USPC .......................................... 568/698; 568/671

(58) Field of Classification Search
CPC .......... C07C 41/01; C07C 41/09; C07C 43/06
USPC ....................................................... 568/671
See application file for complete search history.

(56) References Cited

U.S. PATENT DOCUMENTS

| | | | |
|---|---|---|---|
| 2,021,698 A | 11/1935 | Perkins |
| 2,105,540 A | 1/1938 | Lazier |
| 2,607,807 A | 8/1952 | Ford |
| 2,744,939 A | 5/1956 | Kennel et al. |
| 2,882,244 A | 4/1959 | Milton |
| 3,130,007 A | 4/1964 | Breck |
| 3,478,112 A | 11/1969 | Adam et al. |
| 3,702,886 A | 11/1972 | Argauer et al. |
| 3,729,429 A | 4/1973 | Robson |
| 3,847,756 A | 11/1974 | Statman |
| 3,864,284 A | 2/1975 | Clippinger et al. |
| 3,990,952 A | 11/1976 | Katzen et al. |
| 4,018,514 A | 4/1977 | Plummer |
| 4,065,512 A | 12/1977 | Cares |
| 4,228,307 A | 10/1980 | Zimmerschied |
| 4,270,015 A | 5/1981 | Knifton |
| 4,275,228 A | 6/1981 | Graffaz et al. |
| 4,317,918 A | 3/1982 | Takano et al. |
| 4,374,265 A | 2/1983 | Larkins |
| 4,395,576 A | 7/1983 | Kwantes et al. |
| 4,398,039 A | 8/1983 | Pesa et al. |
| 4,399,305 A | 8/1983 | Schreck |
| 4,421,939 A | 12/1983 | Kiff et al. |
| 4,443,639 A | 4/1984 | Pesa et al. |
| 4,465,854 A | 8/1984 | Pond et al. |
| 4,471,136 A | 9/1984 | Larkins et al. |
| 4,480,115 A | 10/1984 | McGinnis |
| 4,517,391 A | 5/1985 | Schuster et al. |
| 4,521,630 A | 6/1985 | Wattimena et al. |
| 4,550,185 A | 10/1985 | Mabry et al. |
| 4,581,473 A | 4/1986 | Polichnowski et al. |
| 4,613,700 A | 9/1986 | Maki et al. |
| 4,620,050 A | 10/1986 | Cognion et al. |
| 4,670,620 A | 6/1987 | Jacobs et al. |
| 4,678,543 A | 7/1987 | Houben et al. |
| 4,692,218 A | 9/1987 | Houben et al. |
| 4,696,596 A | 9/1987 | Russell et al. |
| 4,777,303 A | 10/1988 | Kitson et al. |
| 4,804,791 A | 2/1989 | Kitson et al. |
| 4,826,795 A | 5/1989 | Kitson et al. |
| 4,843,170 A | 6/1989 | Isshiki et al. |
| 4,886,905 A | 12/1989 | Larkins et al. |
| 4,978,778 A | 12/1990 | Isshiki et al. |
| 4,985,572 A | 1/1991 | Kitson et al. |
| 4,990,655 A | 2/1991 | Kitson et al. |
| 5,008,235 A | 4/1991 | Wegman et al. |
| 5,061,671 A | 10/1991 | Kitson et al. |
| 5,070,016 A | 12/1991 | Hallberg |
| 5,124,004 A | 6/1992 | Grethlein et al. |
| 5,137,861 A | 8/1992 | Shih et al. |
| 5,149,680 A | 9/1992 | Kitson et al. |

(Continued)

FOREIGN PATENT DOCUMENTS

| | | |
|---|---|---|
| CN | 1230458 | 10/1999 |
| CN | 102228831 | 11/2011 |

(Continued)

OTHER PUBLICATIONS

Lee et al. (J. Ind. Eng. Chem., vol. 13, No. 7, Nov. 2007, pp. 1067-1075).*

Zheng, et al., (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al., (2000). Hydrogenation of carbonylic compounds on Pt/SiO2 catalysts modified with SnBu4, Studies in Surface Science and Catalysis, 130, 2063-2068.

(Continued)

*Primary Examiner* — Rosalynd Keys

(57) ABSTRACT

A process for producing of diethyl ether by hydrogenating acetic acid in the presence of a catalyst comprising a first metal on an acidic support, preferably a zeolite support. A preferred catalyst comprises platinum and tin on an acidic support. Selectivities to diethyl ether of at least 60% may be achieved.

15 Claims, No Drawings

(56) References Cited

U.S. PATENT DOCUMENTS

| | | |
|---|---|---|
| 5,155,084 A | 10/1992 | Horn et al. |
| 5,185,308 A | 2/1993 | Bartley et al. |
| 5,227,141 A | 7/1993 | Kim et al. |
| 5,237,108 A | 8/1993 | Marraccini et al. |
| 5,241,106 A | 8/1993 | Inoue et al. |
| 5,243,095 A | 9/1993 | Roberts et al. |
| 5,306,845 A | 4/1994 | Yokohama et al. |
| 5,350,504 A | 9/1994 | Dessau |
| 5,384,296 A * | 1/1995 | Tsao .............................. 502/66 |
| 5,426,246 A | 6/1995 | Nagahara et al. |
| 5,475,144 A | 12/1995 | Watson et al. |
| 5,476,827 A | 12/1995 | Ferrero et al. |
| RE35,377 E | 11/1996 | Steinberg et al. |
| 5,585,523 A | 12/1996 | Kaufhold et al. |
| 5,691,267 A | 11/1997 | Nicolau et al. |
| 5,719,315 A | 2/1998 | Tustin et al. |
| 5,731,456 A | 3/1998 | Tustin et al. |
| 5,767,307 A | 6/1998 | Ramprasad et al. |
| 5,821,111 A | 10/1998 | Grady et al. |
| 5,849,657 A | 12/1998 | Rotgerink et al. |
| 5,861,530 A | 1/1999 | Atkins et al. |
| 5,945,570 A | 8/1999 | Arhancet et al. |
| 5,955,397 A | 9/1999 | Didillon et al. |
| 5,973,193 A | 10/1999 | Crane et al. |
| 6,008,384 A | 12/1999 | Bockrath et al. |
| 6,040,474 A | 3/2000 | Jobson et al. |
| 6,049,008 A | 4/2000 | Roberts et al. |
| 6,114,571 A | 9/2000 | Abel et al. |
| 6,121,498 A | 9/2000 | Tustin et al. |
| 6,232,352 B1 | 5/2001 | Vidalin et al. |
| 6,294,703 B1 | 9/2001 | Hara et al. |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,559,333 B1 | 5/2003 | Brunelle et al. |
| 6,603,038 B1 | 8/2003 | Hagemeyer et al. |
| 6,632,330 B1 | 10/2003 | Colley et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,727,380 B2 | 4/2004 | Ellis et al. |
| 6,765,110 B2 | 7/2004 | Warner et al. |
| 6,768,021 B2 | 7/2004 | Horan et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,074,603 B2 | 7/2006 | Verser et al. |
| 7,084,312 B1 | 8/2006 | Huber et al. |
| 7,297,236 B1 | 11/2007 | Vander Griend |
| 7,351,559 B2 | 4/2008 | Verser et al. |
| 7,375,049 B2 | 5/2008 | Hayes et al. |
| 7,425,657 B1 | 9/2008 | Elliott et al. |
| 7,507,562 B2 | 3/2009 | Verser et al. |
| 7,518,014 B2 | 4/2009 | Kimmich et al. |
| 7,538,060 B2 | 5/2009 | Barnicki et al. |
| 7,553,397 B1 | 6/2009 | Colley et al. |
| 7,572,353 B1 | 8/2009 | Vander Griend |
| 7,585,339 B2 | 9/2009 | Dahl et al. |
| 7,608,744 B1 | 10/2009 | Johnston et al. |
| 7,863,489 B2 | 1/2011 | Johnston et al. |
| 7,884,253 B2 | 2/2011 | Stites et al. |
| 7,994,368 B2 | 8/2011 | Johnston et al. |
| 8,071,821 B2 | 12/2011 | Johnston et al. |
| 8,309,772 B2 | 11/2012 | Weiner et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bharadwaj et al. |
| 2004/0195084 A1 | 10/2004 | Hetherington et al. |
| 2006/0019360 A1 | 1/2006 | Verser et al. |
| 2006/0102520 A1 | 5/2006 | Lapinski et al. |
| 2006/0106246 A1 | 5/2006 | Warner et al. |
| 2006/0127999 A1 | 6/2006 | Verser et al. |
| 2007/0270511 A1 | 11/2007 | Melnichuk et al. |
| 2008/0207953 A1 | 8/2008 | Houssin et al. |
| 2008/0319236 A1 | 12/2008 | McNeff et al. |
| 2009/0005588 A1 | 1/2009 | Hassan et al. |
| 2009/0023192 A1 | 1/2009 | Verser et al. |
| 2009/0081749 A1 | 3/2009 | Verser et al. |
| 2009/0166172 A1 | 7/2009 | Casey |
| 2009/0221725 A1 | 9/2009 | Chornet et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0113843 A1 | 5/2010 | Lee et al. |
| 2010/0121114 A1 | 5/2010 | Weiner et al. |
| 2010/0196789 A1 | 8/2010 | Fisher et al. |
| 2010/0249479 A1 | 9/2010 | Berg-Slot et al. |
| 2011/0065572 A1 | 3/2011 | Olken et al. |
| 2011/0282109 A1 | 11/2011 | Johnston et al. |
| 2012/0253085 A1 | 10/2012 | Johnston et al. |

FOREIGN PATENT DOCUMENTS

| | | |
|---|---|---|
| CN | 102229520 | 11/2011 |
| EP | 0137749 A2 | 4/1985 |
| EP | 0167300 A1 | 1/1986 |
| EP | 0175558 | 3/1986 |
| EP | 0104197 B1 | 5/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0408528 | 7/1990 |
| EP | 0407038 | 1/1999 |
| EP | 0990638 | 4/2000 |
| EP | 1262234 | 12/2002 |
| EP | 1277826 A1 | 1/2003 |
| EP | 2060553 | 5/2009 |
| EP | 2060555 | 5/2009 |
| EP | 2186787 | 5/2010 |
| EP | 2186787 A1 | 5/2010 |
| GB | 1168785 | 10/1969 |
| GB | 1559540 | 1/1980 |
| GB | 2136704 | 9/1984 |
| JP | 6-116182 | 4/1994 |
| JP | 10-306047 A | 11/1998 |
| JP | 11-147845 | 6/1999 |
| JP | 2001-046874 A | 2/2001 |
| JP | 2001-157841 A | 6/2001 |
| WO | WO 83/03409 A1 | 10/1983 |
| WO | WO 03/040037 | 5/2003 |
| WO | WO 2005/102513 | 11/2005 |
| WO | WO 2009/009322 | 1/2009 |
| WO | WO 2009/009323 | 1/2009 |
| WO | WO 2009/063176 | 5/2009 |
| WO | WO 2009/086839 | 7/2009 |
| WO | WO 2009/105860 A1 | 9/2009 |
| WO | WO 2010/014145 | 2/2010 |
| WO | WO 2010/014151 | 2/2010 |
| WO | WO 2010/014153 | 2/2010 |
| WO | WO 2010/055285 A1 | 5/2010 |
| WO | WO 2011/053365 | 5/2011 |

OTHER PUBLICATIONS

Rachmady, Acetic Acid Reduction by H2 on Bimetallic Pt—Fe Catalysts, Journal of Catalysis 209, 87-98 (Apr. 1, 2002), Elsevier Science (USA).

Pestman et al., Reactions of Carboxylic Acids on Oxides, Journal of Catalysis 168:255-264 (1997).

(56) References Cited

OTHER PUBLICATIONS

Pestman et al., Identification of the Active Sites in the Selective Hydrogenation of Acetic Acid to Acetaldehyde on Iron Oxide Catalysts, Journal of Catalysis 174:142-152 (1998).
Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.
Ordóñez et al., The role of metal and support sites on the hydrogenation of acetic acid on Ru-based catalysts, 21ST NAM San Francisco, CA, Jun. 10, 2009.
Gursahani et al., Reaction kinetics measurements and analysis of reaction pathways for conversions of acetic acid, ethanol, and ethyl acetate over silica-supported Pt, Applied Catalysis A: General 222 (2001) 369-392.
Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.
Acala, et al., (2005). Experimental and DFT studies of the conversion of ethanol and acetic acid on PtSn-based catalysts, Journal of Physical Chemistry, 109(6), 2074-2085.
International Search Report and Written Opinion for PCT/US2009/004197 mailed Mar. 24, 2010 (14 pages).
International Search Report and Written Opinion for PCT/US2009/004195 mailed Mar. 26, 2010 (12 pages).
T. Yokoyama, et al., "Carboxylic Acids and Derivatives", Fine Chemicals through Heterogenous Catalysis, pp. 370-379.
Spivey et al., "Heterogeneous catalytic synthesis of ethanol from biomass-dervied syngas," Chemical Society Review, 2007, vol. 36, pp. 1514-1528.
Rodrigues and Bueno, "Co/SiO2 catalysts for selective hydrogenation of crotonaldehyde: III. Promoting effect of zinc," Applied Catalysis A: General (2004), 257, p. 210-211.
Nitta, et al. "Selective hydrogenation of αβ-unsaturated aldehydes on cobalt—silica catalysts obtained from cobalt chrysotile," Applied Catal. (1989), 56, p. 9-22.
Liberkova, and Tourounde, "Performance of Pt/SnO2 catalyst in the gas phase hydrogenation of crotonaldehyde," J. Mol. Catal. A: Chemical (2002), 180, p. 221-230.
Consonni, et al. "High Performances of Pt/ZnO Catalysts in Selective Hydrogenation of Crotonaldehyde," J. Catal. (1999), 188, p. 165-175.
Ammari, et al. "An emergent catalytic material: Pt/ZnO catalyst for selective hydrogenation of crotonaldehyde," J. Catal. (2004), 221, p. 32-42.
Ammari, et al. "Selective hydrogenation of crotonaldehyde on Pt/ZnCl2/SiO2 catalysts," J. Catal. (2005), 235, p. 1-9.
Written Opinion for PCT/US2010/054132 mailed Nov. 29, 2011.
International Preliminary Report on Patentability mailed Feb. 1, 2012 in corresponding International Application No. PCT/US2010/054132.
International Search Report and Written Opinion for PCT/US2010/054134 mailed Feb. 28, 2011.
International Search Report and Written Opinion for PCT/US2010/022950 mailed Sep. 7, 2011.
International Search Report and Written Opinion for PCT/US2010/022947 mailed Jun. 7, 2010.
International Search Report and Written Opinion for PCT/US2010/022949 mailed Jun. 7, 2010.
International Search Report and Written Opinion for PCT/US2010/022950 mailed Jun. 15, 2010.
International Search Report and Written Opinion for PCT/US2010/022953 mailed Jun. 7, 2010.
International Preliminary Report on Patentability mailed on May 18, 2012 in corresponding International Application No. PCT/US2010/054136.
International Search Report and Written Opinion mailed on May 22, 2012 in corresponding International Application No. PCT/US2012/031207.
Minglin Xiang et al., "XPS study of potassium-promoted molybdenum carbides for mixed alcohols synthesis via CO hydrogenation", Journal of Natural Gas Chemistry, vol. 19, 2010, pp. 151-155.
Domine, D. et al., Mol. Sieves Pap. Conf., 1967, 78 Soc. Chem. Ind. London.
Subramani, et al., "A Review of Recent Literature to Search for an Efficient Catalytic Process for the Conversion of Syngas to Ethanol," Energy & Fuels, 2008, vol. 22, pp. 814-839.
Pestman et al., The formation of ketones and aldehydes from carboxylic acids, structure-activity relationship for two competitive reactions, Journal of Molecular Catalysis A: Chemical 103 Jun. 14, 1995, 175-180.
Proc. Roy Soc. A314, pp. 473-498 (1970).
International Search Report and Written Opinion for PCT/US2010/054132 mailed Feb. 28, 2011.
Nefedov and I V Mishin B K, "Synthesis of diethyl ether in presence of zeolite catalysts", Russian Chem. Bull., Springer Anew York LLC, v. 28, Jan. 1, 1979, pp. 183-186.
Jingfa D et al., "Acidic properties of ZSM-5 zeolite and conversion of ethanol to diethyl ether," Applied Catalyst, v. 41, Jan. 1, 1988, pp. 13-22.
Brunauer Emmett and Teller, J. Am. Chem. Soc. 60, 309 (1938).
Final Office Action for U.S. Appl. No. 13/179,955 dated Oct. 24, 2012.
Office Action for U.S. Appl. No. 12/699,024 dated Nov. 29, 2012.
Office Action for U.S. Appl. No. 12/698,947 dated Dec. 12, 2012.
Office Action for U.S. Appl. No. 12/698,968 dated Dec. 18, 2012.

* cited by examiner

PROCESS FOR MAKING DIETHYL ETHER FROM ACETIC ACID

CROSS REFERENCE TO RELATED APPLICATIONS

This application is a continuation-in-part application of U.S. application Ser. No. 12/588,727, filed Oct. 26, 2009, and claims the priority to U.S. Provisional Application No. 61/300,812, filed Feb. 2, 2010, priorities of which is hereby claimed and the entire contents and disclosures of which are incorporated herein by reference.

FIELD OF THE INVENTION

The present invention relates generally to processes for hydrogenating acetic acid to form diethyl ether and to novel catalysts for use in such processes, the catalysts having high selectivities for diethyl ether.

BACKGROUND OF THE INVENTION

Diethyl ether finds various uses as a solvent, anesthesia, and fuel. Currently diethyl ether is produced as a byproduct of the dehydration of ethanol to make ethylene using sulfuric acid, as described in U.S. Pat. Nos. 7,585,339, 5,227,141 and 3,847,756. Typically diethyl ether is favored in the dehydration at lower reaction temperatures, but a mixture of ethylene and diethyl ether is still present. Other processes, such as those described in U.S. Pat. No. 4,670,620, have sought to increase selectivity in the dehydrating reaction of ethanol towards ethylene by using a zeolite at elevated temperatures.

Further, ethanol is conventionally produced from feedstocks where price fluctuations are becoming more significant. That is, fluctuating natural gas and crude oil prices contribute to fluctuations in the cost of conventionally produced petroleum, natural gas or corn or, other agricultural product-sourced ethanol, thus creating the need for reactants other than ethanol.

Therefore, the need exists for a method for directly producing diethyl ether and for producing diethyl ether on a commercial scale from a non-alcohol source.

SUMMARY OF THE INVENTION

The present invention is directed to processes for making diethyl ether by hydrogenating acetic acid, preferably at high diethyl ether selectivity.

In a first embodiment, the invention is a process for producing diethyl ether comprising hydrogenating acetic acid in the presence of a catalyst comprising a first metal on an acidic support selected from the group consisting of (i) a zeolite support, (ii) a support selected from the group consisting of iron oxide, alumina, silica/aluminas, titania, and zirconia, and (iii) a support modified with an acidic and/or redox modifier.

In a second embodiment, the invention is a process for producing diethyl ether comprising hydrogenating acetic acid in the presence of a catalyst comprising a first metal on a zeolite support.

Preferably any of the acidic supports may also be modified with an acidic and/or redox modifier. Suitable modifiers include oxides of Group IVB metals, oxides of Group VB metals, oxides of Group VIB metals, iron oxides, aluminum oxides, and mixtures thereof. More particularly the modifiers are selected from the group consisting of $WO_3$, $MoO_3$, $Fe_2O_3$, $Cr_2O_3$, $V_2O_5$, $MnO_2$, $CuO$, $CO_2O_3$, $Bi_2O_3$, $TiO_2$, $ZrO_2$, $Nb_2O_5$, $Ta_2O_5$, $Al_2O_3$, $B_2O_3$, $P_2O_5$, and $Sb_2O_3$.

In a preferred embodiment, the invention is a process for producing diethyl ether comprising hydrogenating acetic acid in the presence of a catalyst comprising a first metal on a zeolite support. The catalyst may further comprise a second and/or third metal.

Preferably, the first metal is selected from the group consisting of Group IB, IIB, IIIB, IVB, VB, VIIB, VIIB, or VIII transitional metal, a lanthanide metal, an actinide metal or a metal from any of Groups IIIA, IVA, VA, or VIA and more preferably the first metal is selected from the group consisting of copper, iron, cobalt, nickel, ruthenium, rhodium, palladium, osmium, iridium, platinum, titanium, zinc, chromium, rhenium, molybdenum, and tungsten. Preferably, the second metal, which is different than the first metal, is selected from the group consisting of copper, molybdenum, tin, chromium, iron, cobalt, vanadium, tungsten, palladium, platinum, lanthanum, cerium, manganese, ruthenium, rhenium, gold, and nickel. One preferred catalyst comprises platinum and tin.

The zeolite support is selected from the group consisting of mordenites, ZSM-5, a zeolite X, and a zeolite Y. Preferably, the zeolite support is present in an amount of 75 wt. % to 99.9 wt. %, based on the total weight of the catalyst.

In one embodiment the hydrogenation is performed in a vapor phase at a temperature of from 125° C. to 350° C., a pressure of 10 KPa to 3000 KPa, and a hydrogen to acetic acid mole ratio of greater than 4:1.

In one embodiment the conversion of acetic acid is at least 10% and the selectivity to diethyl ether is at least 60%. In preferred embodiments, the selectivity is at least 70% or at least 80%. Preferably, the selectivity to methane, ethane, and carbon dioxide, and mixtures thereof is less than 4%.

DETAILED DESCRIPTION OF THE INVENTION

In general the present invention relates to processes for producing diethyl ether by hydrogenation acetic acid in the presence of a catalyst. Without being bound to theory, the hydrogenation reaction is believed to be as follows:

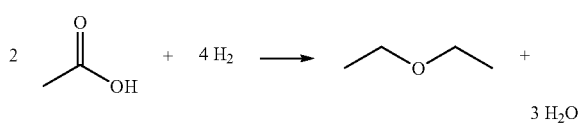

Such a reaction is surprising and unexpected because most literature on the hydrogenation of carboxylic acids reports producing not ethers, but alcohols, as described in U.S. Pat. Nos. 3,478,112, 4,317,918, 4,398,039, 4,443,639, 4,480,115, and 4,517,391. Other literature reports hydrogenation of carboxylic acids to form esters, U.S. Pat. No. 4,275,228, and aldehydes, as described in U.S. Pat. No. 5,306,845, and U.S. Pat. No. 5,476,827.

In one embodiment the catalyst comprises at least one metal and acidic support, such as a zeolite support or a support modified with an acidic and/or redox modifier. Without being bound to theory diethyl ether production may be favored when the support is acidic. Supports that are not acidic enough to favor diethyl ether may favor other ester compounds and ethylene. The present invention also relates to such catalysts and processes for making the catalysts. Using these catalysts in the hydrogenation of acetic acid provides high selectivities to diethyl ether, which allows embodiments of the present invention to be used in industrial operations to produce diethyl ether on an economically feasible scale.

The catalyst of the invention comprises a first metal and optionally one or more of a second metal, a third metal, or additional metals. In this context, the numerical terms "first," "second," "third," etc., when used to modify the word "metal," are meant to indicate that the respective metals are different from one another. The total weight of all metals present in the catalyst preferably is from 0.1 to 25 wt. %, e.g., from 0.5 to 15 wt. %, or from 0.75 to 10 wt. %. For purposes of the present specification, unless otherwise indicated, weight percent is based on the total weight the catalyst including metal and support. The metal(s) in the catalyst may be present in the form of one or more metal oxides. For purposes of determining the weight percent of the metal(s) in the catalyst, the weight of any oxygen that is bound to the metal is ignored.

The first metal may be a Group IB, IIB, IIIB, IVB, VB, VIIB, VIIB, or VIII transitional metal, a lanthanide metal, an actinide metal, or a metal from any of Groups IIIA, IVA, VA, or VIA. In a preferred embodiment, the first metal is selected the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises the platinum in an amount less than 5 wt. %, e.g. less than 3 wt. % or less than 1 wt. %, due to the availability and cost of platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

Where the catalyst includes two or more metals, one metal may act as a promoter metal and the other metal is the main metal. For instance, with a platinum/tin catalyst, platinum may be considered to be the main metal and tin may be considered the promoter metal. For convenience, the present specification refers to the first metal as the primary catalyst and the second metal (and optional metals) as the promoter(s). This should not be taken as an indication of the underlying mechanism of the catalytic activity.

If the catalyst includes two or more metals, e.g., a first metal and a second metal, the first metal optionally is present in the catalyst in an amount from 0.1 to 10 wt. %, e.g. from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. The mole ratio of the first metal to the second metal preferably is from 10:1 to 1:10, e.g., from 4:1 to 1:4, from 2:1 to 1:2, from 1.5:1 to 1:1.5 or from 1.1:1 to 1:1.1. In one embodiment, the catalyst comprises platinum and tin in a 1:1 molar ratio. For catalysts comprising two or more metals, the two or more metals may be alloyed with one another or may comprise a non-alloyed metal solution or mixture.

In embodiments when the catalyst comprises a third metal, the third metal may be selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the second metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In one embodiment, the catalyst comprises a first metal and no additional metals (no second metal, etc.). In this embodiment, the first metal preferably is present in an amount from 0.1 to 25 wt. %, e.g., from 0.1 to 10 wt. %, or from 1 to 5 wt. %. In another embodiment, the catalyst comprises a combination of two or more metals on a support. Specific preferred metal compositions for various catalysts of this embodiment of the invention are provided below in Table 1. Where the catalyst comprises a first metal and a second metal, the first metal preferably is present in an amount from 0.1 to 5 wt. % and the second metal preferably is present in an amount from 0.1 to 5 wt. %. Where the catalyst comprises a first metal, a second metal and a third metal, the first metal preferably is present in an amount from 0.1 to 5 wt. %, the second metal preferably is present in an amount from 0.1 to 5 wt. %, and the third metal preferably is present in an amount from 0.1 to 2 wt. %. Where the first metal is platinum, the first metal preferably is present in an amount from 0.1 to 3 wt. %, the second metal is present in an amount from 0.1 to 5 wt. %, and the third metal, if present, preferably is present in an amount from 0.1 to 2 wt. %.

TABLE 1

EXEMPLARY METAL COMBINATIONS FOR CATALYSTS

| First Metal | Second Metal | Third Metal | First Metal | Second Metal | Third Metal |
|---|---|---|---|---|---|
| Cu | Ag |  | Pt | Co |  |
| Cu | Cr |  | Pt | Cr |  |
| Cu | V |  | Pt | Cu |  |
| Cu | W |  | Pt | Fe |  |
| Cu | Zn |  | Pt | Mo |  |
| Ni | Au |  | Pt | Sn |  |
| Ni | Re |  | Pt | Sn | Co |
| Ni | V |  | Pt | Sn | Re |
| Ni | W |  | Pt | Sn | Ru |
| Pd | Co |  | Pt | Sn | Pd |
| Pd | Cr |  | Rh | Cu |  |
| Pd | Cu |  | Rh | Ni |  |
| Pd | Fe |  | Ru | Co |  |
| Pd | La |  | Ru | Cr |  |
| Pd | Mo |  | Ru | Cu |  |
| Pd | Ni |  | Ru | Fe |  |
| Pd | Re |  | Ru | La |  |
| Pd | Sn |  | Ru | Mo |  |
| Pd | V |  | Ru | Ni |  |
| Pd | W |  | Ru | Sn |  |

Depending primarily on how the catalyst is manufactured, the metals of the catalysts of the present invention may be dispersed throughout the support, coated on the outer surface of the support (egg shell), or decorated on the surface of the support.

In one embodiment, catalysts of the present invention further comprise an acidic support selected from the group consisting of (i) zeolite supports, (ii) supports selected from the group consisting of iron oxide, alumina, silica/aluminas, titania, and zirconia, and (iii) supports modified with acidic and/or redox modifiers. In one embodiment the catalyst preferably comprises a zeolite support. Various zeolites and zeolite-type materials are known in the art for the catalysis of chemical reactions. Suitable zeolite supports include those selected from the group consisting of mordenites, ZSM-5, a zeolite X and a zeolite Y. The preparation of large-pore mordenites is described, for example, in U.S. Pat. No. 4,018,514 and in Mol. Sieves Pap. Conf., 1967, 78, Soc. Chem. Ind. London, by D. DOMINE and J. QUOBEX, the entire contents and disclosure of which are hereby incorporated by reference. Zeolite X is described, for example, in U.S. Pat. No. 2,882,244 and zeolite Y in U.S. Pat. No. 3,130,007, the entire contents and disclosure of which are hereby incorporated by reference. U.S. Pat. No. 3,702,886, the entire contents and disclosure of which is hereby incorporated by reference, discloses a class of synthetic zeolites, characterized as "Zeolite ZSM-5," which are effective for the catalysis of various hydrocarbon conversion processes.

Suitable zeolites may be in the partially or totally acidified form, or in the partially dealuminated form.

In one exemplary embodiment, the zeolite supports may be characterized as "H-ZSM-5" or "H-mordenite" zeolites are prepared from a corresponding "ZSM-5" zeolite or "mordenite" zeolite by replacing most, and generally at least about 80%, of the cations of the latter zeolite with hydrogen ions using techniques well-known in the art. These zeolite supports are essentially crystalline aluminosilicates or, when in the neutral form, are a combination of silica and alumina in a well defined crystalline structure. In a particularly preferred class of zeolite supports, the molar ratio of $SiO_2$ to $Al_2O_3$ in the zeolites is within the range of from 10 to 60, e.g., from 10 to 50, or from 20 to 50.

The total weight of the zeolite support is typically from 75 wt. % to 99.9 wt. %, e.g., from 78 wt. % to 97 wt. %, or from 80 wt. % to 95 wt. %, based on the weight of the catalyst.

Other suitable supports include iron oxide, silica, alumina, silica/aluminas, titania, zirconia, carbon, graphite, high surface area graphitized carbon, activated carbons, and mixtures thereof. Preferred acidic supports are selected from the group consisting of iron oxide, alumina, silica/aluminas, titania, zirconia, and mixtures thereof.

The supports of the present invention, including zeolite supports, optionally comprise a acidic and/or redox support modifier that, for example, may be selected from the group consisting of: oxides of Group IVB metals, oxides of Group VB metals, oxides of Group VIB metals, iron oxides, aluminum oxides, and mixtures thereof. In one embodiment, acidic and/or redox modifiers may be added to supports that are less acidic, such as silica, carbon, graphite, high surface area graphitized carbon, activated carbons, and mixtures thereof. The support modifier preferably is an acidic and/or redox modifier having a low volatility or is non-volatile. Low volatility modifiers have a rate of loss that is low enough such that the acidity of the support modifiers is not reversed during the life of the catalyst. Preferably, redox support modifiers are selected from the group consisting of $WO_3$, $MoO_3$, $Fe_2O_3$, $Cr_2O_3$, $V_2O_5$, $MnO_2$, $CuO$, $CO_2O_3$, $Bi_2O_3$. Preferably, acidic support modifiers are selected from the group consisting of $TiO_2$, $ZrO_2$, $Nb_2O_5$, $Ta_2O_5$, $Al_2O_3$, $B_2O_3$, $P_2O_5$, and $Sb_2O_3$. In preferred embodiments, the acidic and/or redox support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

The catalyst compositions of the invention preferably are formed through metal impregnation of the acidic support, such as a zeolite support or modified support. Before the metals are impregnated, it typically is desired to form the modified support, if necessary, through a step of impregnating the support material with the support modifier. A precursor to the support modifier, such as an acetate or nitrate, may be used. In one aspect, the support modifier, e.g., $WO_3$ or $TiO_2$, is added to the support material, e.g., $SiO_2$. For example, an aqueous suspension of the support modifier may be formed by adding the solid support modifier to deionized water, followed by the addition of colloidal support material thereto. The resulting mixture may be stirred and added to additional support material using, for example, incipient wetness techniques in which the support modifier is added to a support material having the same pore volume as the volume of the support modifier solution. Capillary action then draws the support modifier into the pores in the support material. The modified support can then be formed by drying and calcining to drive off water and any volatile components within the support modifier solution and depositing the support modifier on the support material. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours. Once formed, the modified supports may be shaped into particles having the desired size distribution, e.g., to form particles having an average particle size in the range of from 0.2 to 0.4 cm. The supports may be extruded, pelletized, tabletized, pressed, crushed or sieved to the desired size distribution. Any of the known methods to shape the support materials into desired size distribution can be employed. Calcining of the shaped modified support may occur, for example, at a temperature of from 250° C. to 800° C., e.g., from 300 to 700° C. or about 500° C., optionally for a period of from 1 to 12 hours, e.g., from 2 to 10 hours, from 4 to 8 hours or about 6 hours.

In a preferred method of preparing the catalyst, the metals are impregnated onto the acidic supports. A precursor of the first metal (first metal precursor) preferably is used in the metal impregnation step, such as a water soluble compound or water dispersible compound/complex that includes the first metal of interest. Depending on the metal precursor employed, the use of a solvent, such as water, glacial acetic acid or an organic solvent, may be preferred. The second metal also may be impregnated into the acidic support from a second metal precursor. If desired, a third metal may also be impregnated into the acidic support.

Impregnation occurs by adding, optionally drop wise, either or both the first metal precursor and/or the second metal precursor and/or additional metal precursors, preferably in suspension or solution, to the dry support. The resulting mixture may then be heated, e.g., optionally under vacuum, in order to remove the solvent. Additional drying and calcining may then be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the first and second metals (and optional additional metals) into the acidic support may occur simultaneously (co-impregnation) or sequentially. In simultaneous impregnation, the first and second metal precursors (and optionally additional metal precursors) are mixed together and added to the acidic support together, followed by drying and calcination to form the final catalyst composition. With simultaneous impregnation, it may be desired to employ a solubilizing agent, e.g., ammonium oxalate, to facilitate solubilizing of the first and second metal precursors in the event the two precursors are incompatible with the desired solvent, e.g., water.

In sequential impregnation, the first metal precursor is first added to the acidic support followed by drying and calcining, and the resulting material is then impregnated with the second metal precursor followed by an additional drying and calcining step to form the final catalyst composition. Additional metal precursors (e.g., a third metal precursor) may be added either with the first and/or second metal precursor or an a separate third impregnation step, followed by drying and calcination. Of course, combinations of sequential and simultaneous impregnation may be employed if desired.

Suitable metal precursors include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride. Generally, both from the point of view of economics and environmental aspects, aqueous solutions of soluble compounds of platinum are preferred. In one embodiment, the first metal precursor is not a metal halide and is substantially free of metal halides.

In one aspect, the "promoter" metal or metal precursor is first added to the acidic support, followed by the "main" or "primary" metal or metal precursor. Of course the reverse order of addition is also possible. Exemplary precursors for promoter metals include metal halides, amine solubilized metal hydroxides, metal nitrates, or metal oxalates. As indicated above, in the sequential embodiment, each impregnation step preferably is followed by drying and calcination. In the case of promoted bimetallic catalysts as described above, a sequential impregnation may be used, starting with the addition of the promoter metal followed by a second impregnation step involving co-impregnation of the two principal metals, e.g., Pt and Sn.

The process of the invention may be conducted in a variety of configurations using a fixed bed reactor or a fluidized bed reactor as one of skill in the art will readily appreciate. In many embodiments of the present invention, an "adiabatic" reactor can be used; that is, there is little or no need for internal plumbing through the reaction zone to add or remove heat. Alternatively, a shell and tube reactor provided with a heat transfer medium can be used. In many cases, the reaction zone may be housed in a single vessel or in a series of vessels with heat exchangers therebetween. It is considered significant that acetic acid reduction processes using the catalysts of the present invention may be carried out in adiabatic reactors as this reactor configuration is typically far less capital intensive than tube and shell configurations.

Typically, the catalyst is employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably the reaction is carried out in the vapor phase under the following conditions. The reaction temperature may the range from of 125° C. to 350° C., e.g., from 200° C. to 325° C., from 225° C. to about 300° C., or from 250° C. to about 300° C. The pressure may range from 10 KPa to 3000 KPa (about 0.1 to 30 atmospheres), e.g., from 50 KPa to 2300 KPa, or from 100 KPa to 1500 KPa. The reactants may be fed to the reactor at a gas hourly space velocities (GHSV) of greater than 500 $hr^{-1}$, e.g., greater than 1000 $hr^{-1}$, greater than 2500 $hr^{-1}$ and even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

In another aspect of the process of this invention, the hydrogenation is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes four moles of hydrogen per every two moles of acetic acid to produce one mole of diethyl ether, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 4:1, e.g., greater than 5:1 or greater than 10:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The acetic acid may be vaporized at the reaction temperature, and then the vaporized acetic acid can be fed along with hydrogen in undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid.

In particular, using catalysts and processes of the present invention may achieve favorable conversion of acetic acid and favorable selectivity and productivity to diethyl ether. For purposes of the present invention, the term conversion refers to the amount of acetic acid in the feed that is converted to a compound other than acetic acid. Conversion is expressed as a mole percentage based on acetic acid in the feed. The conversion of acetic acid (AcOH) is calculated from gas chromatography (GC) data using the following equation:

$$AcOH\ Conv.\ (\%) = 100 * \frac{mmol\ AcOH\ (feed\ stream) - mmol\ AcOH\ (GC)}{mmol\ AcOH\ (feed\ stream)}$$

For purposes of the present invention, the conversion may be at least 10%, e.g., at least 20%, at least 40%, at least 50%, at least 60%, or at least 70% or at least 80%. Although catalysts that have high conversions are desirable, such as at least 80% or at least 90%, a low conversion may be acceptable at high selectivity to diethyl ether. It is, of course, well understood that in many cases, it is possible to compensate for conversion by appropriate recycle streams or use of larger reactors, but it is more difficult to compensate for poor selectivity.

"Selectivity" is expressed as a mole percent based on converted acetic acid. It should be understood that each compound converted from acetic acid has an independent selectivity and that selectivity is independent from conversion. For example, if 50 mole % of the converted acetic acid is converted to diethyl ether, we refer to the diethyl ether selectivity as 50%. Selectivity to diethyl ether (Et$_2$O) is calculated from gas chromatography (GC) data using the following equation:

$$Et_2O\ Sel.\ (\%) = 100 * \frac{mmol\ Et_2O\ (GC)}{\frac{Total\ mmol\ C\ (GC)}{2} - mmol\ AcOH\ (feed\ stream)}$$

wherein "Total mmol C (GC)" refers to total mmols of carbon from all of the products analyzed by gas chromatograph.

For purposes of the present invention, the selectivity to diethyl ether of the catalyst is at least 60%, e.g., at least 70%, or at least 80%. Preferably, the selectivity to diethyl ether is at least 75%, e.g., at least 80% or at least 90%. In embodiments of the present invention is also desirable to have low selectivity to undesirable products, such as methane, ethane, and carbon dioxide. The selectivity to these undesirable products is less than 4%, e.g., less than 2% or less than 1%. Preferably, no detectable amounts of these undesirable products are formed during hydrogenation. In several embodiments of the present invention, formation of alkanes is low, usually under 2%, often under 1%, and in many cases under 0.5% of the acetic acid passed over the catalyst is converted to alkanes, which have little value other than as fuel.

Productivity refers to the grams of a specified product, e.g., diethyl ether, formed during the hydrogenation based on the kilograms of catalyst used per hour. For purposes of the present invention, a productivity of at least 200 grams of diethyl ether per kilogram catalyst per hour, e.g., at least 400 grams of diethyl ether or at least 600 grams of diethyl ether, is preferred. In terms of ranges, the preferred productivity to diethyl ether is from 200 to 3,000 grams of diethyl ether per kilogram catalyst per hour, e.g., from 400 to 2,500 grams of diethyl ether per kilogram catalyst per hour or from 600 to 2,000 grams of diethyl ether per kilogram catalyst per hour.

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352 to Vidalin, the disclosure of which is incorporated herein by reference in its entirety, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, the process can also be used to make hydrogen which may be utilized in connection with this invention.

U.S. Pat. No. RE 35,377 to Steinberg et al., also incorporated herein by reference in its entirety, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. See also U.S. Pat. No. 5,821,111 to Grady et al., which discloses a process for converting waste biomass through gasification into synthesis gas as well as U.S. Pat. No. 6,685,754 to Kindig et al., the disclosures of which are incorporated herein by reference in their entireties.

Alternatively, acetic acid in vapor form may be taken directly as crude product from the flash vessel of a methanol carbonylation unit of the class described in U.S. Pat. No. 6,657,078 to Scates et al., the entirety of which is incorporated herein by reference in its entirety. The crude vapor product, for example, may be fed directly to the diethyl ether synthesis reaction zones of the present invention without the need for condensing the acetic acid and light ends or removing water, saving overall processing costs.

The following examples describe the procedures used for the preparation of various catalysts employed in the process of this invention.

EXAMPLES

Example 1

Vaporized acetic acid (0.09 g/min HOAc) and hydrogen (160 sccm/min H$_2$; 60 sccm/min N$_2$) at a pressure of 677.4 KPa (200 psig) were passed over a hydrogenation catalyst of the present invention comprising 3 wt. % Pt and 1.8 wt. % Sn on a support comprising hydrogen form ZSM-5 molecular sieve at a temperature of 250° C., GHSV of 6570 h$^{-1}$ and 12 h of time on stream (TOS). Diethyl ether was obtained at a selectivity of 96% and a productivity of 2646 g/kg/h accompanied by 4% selectivity to ethyl acetate with 22% conversion.

Example 2

Comparative 2.5 ml solid catalyst comprising Pt(3%)-Sn(1.8%) on a KA160 (SiO$_2$—Al$_2$O$_3$) support (14/30 mesh, diluted 1:1 (v/v, with quartz chips, 14/30 mesh) was reacted under the following conditions: pressure of =1400 KPa (200 psig); temperature=250° C.; 0.09 g/min HOAc; 120 sccm/min H$_2$; 60 sccm/min N$_2$; GHSV=6570 h$^{-1}$; and 24 h of time on stream (TOS). No diethyl ether was detected in the crude product.

Example 3

Comparative 2.5 ml solid catalyst comprising Pt(3%)-Sn(1.8%) on a SiO$_2$ support modified with 10% of TiO$_2$ (14/30 mesh, diluted 1:1 (v/v, with quartz chips, 14/30 mesh) was reacted under the following conditions: pressure of =1400 KPa (200 psig); temperature=250° C.; 0.09 g/min HOAc; 120 sccm/min H$_2$; 60 sccm/min N$_2$; GHSV=6570 h$^{-1}$; and 24 h of time on stream (TOS). No diethyl ether was detected in the crude product.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing diethyl ether comprising:
hydrogenating acetic acid in the presence of a catalyst comprising platinum and tin on a hydrogen form ZSM-5 molecular sieve support;
wherein selectivity of acetic acid to diethyl ether is at least 60%.

2. The process of claim 1, wherein the support is present in an amount of 75 wt. % to 99.9 wt. %, based on the total weight of the catalyst.

3. The process of claim 1, wherein the support further comprises a modifier selected from the group consisting of oxides of Group IVB metals, oxides of Group VB metals, oxides of Group VIB metals, iron oxides, aluminum oxides, and mixtures thereof.

4. The process of claim 1, wherein the support further comprises a modifier selected from the group consisting of $WO_3$, $MoO_3$, $Fe_2O_3$, $Cr_2O_3$, $V_2O_5$, $MnO_2$, $CuO$, $Co_2O_3$, $Bi_2O_3$.

5. The process of claim 1, wherein the support further comprises a modifier selected from the group consisting of $TiO_2$, $ZrO_2$, $Nb_2O_5$, $Ta_2O_5$, $Al_2O_3$, $B_2O_3$, $P_2O_5$, and $Sb_2O_3$.

6. The process of claim 1, wherein the platinum is present in an amount of from 0.1 to 25 wt. %, based on the total weight of the catalyst.

7. The process of claim 1, wherein the tin is present in an amount of from 0.1 to 10 wt. %, based on the total weight of the catalyst.

8. The process of claim 1, wherein the catalyst further comprises a third metal different from the first and second metals.

9. The process of claim 8, wherein the third metal is selected from the group consisting of cobalt, palladium, ruthenium, copper, zinc, and rhenium.

10. The process of claim 8, wherein the third metal is present in an amount of 0.05 and 4 wt. %, based on the total weight of the catalyst.

11. The process of claim 1, wherein at least 10% of the acetic acid is converted during hydrogenation.

12. The process of claim 1, wherein the hydrogenation has a selectivity to diethyl ether of at least 70%.

13. The process of claim 1, wherein the hydrogenation has a selectivity to methane, ethane, and carbon dioxide and mixtures thereof is less than 4%.

14. The process of claim 1, wherein the acetic acid is obtained from a coal source, natural gas source or biomass source.

15. The process of claim 1, wherein the hydrogenation is performed in a vapor phase at a temperature of from 125° C. to 350° C., a pressure of 10 kPa to 3000 kPa, and a hydrogen to acetic acid mole ratio of greater than 4:1.

* * * * *